US00PP14483P29

(12) United States Plant Patent
Sherman et al.

(10) Patent No.: US PP14,483 P2
(45) Date of Patent: Jan. 27, 2004

(54) PEACH TREE NAMED 'GULFKING'

(50) Latin Name: *Prunus persica*
Varietal Denomination: Gulfking

(75) Inventors: Wayne B. Sherman, Gainesville, FL (US); Gerard W. Krewer, Tifton, GA (US); Thomas G. Beckman, Byron, GA (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 10/329,004

(22) Filed: Dec. 26, 2002

(51) Int. Cl.[7] ..... A01H 5/00
(52) U.S. Cl. ..... Plt./197

(58) Field of Search ..... Plt./197

*Primary Examiner*—Bruce R. Campell
*Assistant Examiner*—Susan B. McCormick

(57) ABSTRACT

A new and distinct variety of peach tree which has a low winter chilling requirement of approximately 350 chill units (cu). The tree is of large size, is highly vigorous with a semi-spreading growth habit. The tree has showy pink flowers and reniform leaf glands. Trees of 'Gulfking' are self-fertile and regularly bear heavy annual crops which are moderate size for the early ripening season. Fruit have yellow, very firm, non-melting and clingstone flesh. Fruit are uniform, attractive, substantially symmetrical shape, and have an attractive normally 80 to 90% red skin with moderately red stripes from tip to shoulder over a deep yellow ground color. The fruit ripens with 'Flordaking' in early May at Attapulgus, Ga.

1 Drawing Sheet

BACKGROUND OF THE NEW VARIETY

The present invention relates to a new and distinct variety of peach (*Prunus persica* (L.) Batsch) tree which is named 'Gulfking' and, more particularly to a peach tree which produces an attractive, high percentage red skin, good eating quality fruit which are clingstone, non-melting flesh. The fruit mature for the fresh market in early May at Attapulgus, Ga. on a tree adapted to a mid-chill winter climate. Contrast is made to 'Flordaking' (nonpatented) peach tree, a standard variety, for reliable description. This new variety is a promising candidate for commercial success in that it retains fruit firmness at the full flavor, tree ripe stage for 7 to 10 days on the tree.

ORGIN OF THE VARIETY

'Gulfking' peach tree (genotype) originated in a cultivated area of the fruit breeding program located at Attapulgus. The seed parent was BY87P285 (nonpatented), a non-melting flesh peach and the pollen parent was 'UFGold' (U.S. Plant Pat. No. 10,315). BY87P285 originated from a hybrid of 'Sunprince' (nonpatented) and L78-8-14 (nonpatented). L78-8-14 originated from a hybrid of 'Harvester' (nonpatented)×'Majestic' (nonpatented). 'Gulfking' peach tree was selected in 1998, and was designated AP 98-4. It was propagated by budding on 'Flordaguard' (nonpatented) and 'Nemared' (nonpatented) seedling rootstock (for root-knot nematode control) and determined at Attapulgus to have unique tree and fruit characteristics making it worthy for commercial fresh fruit production. There are no known effects of either rootstock on this scion cultivar. Asexually propagated plants remained true to the original tree as all characteristics of the tree and the fruit were transmitted.

SUMMARY OF THE VARIETY

'Gulfking' peach tree is a new and distinct variety that bears yellow, non-melting flesh fruit, and has a moderate-chilling dormancy requirement. It blooms with 'Flordaking' peach tree at Attapulgus, bearing red skin and yellow flesh fruit. The estimated chilling requirement is 350 chill units.

The present invention resulting in 'Gulfking' peach tree is characterized by non-melting flesh fruit of excellent flavor and eating quality on a tree adapted to mild winters. The trees are vigorous, productive and without alternate bearing. Trees attain in two years, a height of three meters and a spread of two meters at Attapulgus. Terminal growth of up to a meter annually is common on mature 4-year-old trees with normal pruning to a vase shape. The first fruit ripen in early May at Attapulgus or in about 75 days from full bloom which the same time as 'Flordaking' peach tree. The fruit are uniform in size and moderately large for an early peach averaging 120 g or about 2⅜ inches in diameter. Ripe fruit have 80 to 90% red skin with moderately fine darker red stripes from the tip to the shoulder. There is no red in flesh at the pit, but fruit have some red pigment flecks in the outer flesh on the sun exposed side of the fruit. The flower petals are pink and showy. The anthers are light red.

DESCRIPTION OF THE DRAWING

The accompanying drawing is a color photograph which shows a typical specimen of the fruit, leaf, and stem of the new variety as nearly true as it is reasonably possible to make in a color illustration of this type.

The photograph also shows a near round fruit shape and an attractive exterior coloration. Six fruit specimens are shown above a ruler in a stem end view, a blossom end view, side views facing and perpendicular to the suture, and fruit cut at the equator showing the flesh with and without a pit in place.

DETAILED BOTANICAL DESCRIPTION

The tree, flowers, and fruit may vary in slight detail due to variations in soil type, cultural practices, and climatic condition. The potential for commercial production of fresh fruit by 'Gulfking' peach tree is high, due to its attractive red skin, yellow ground color, early ripening, good flavor balance of sugar and acid, and exceptional firmness due to its non-melting flesh. The present botanical description is that of the variety as grown on 4-year-old trees on 'Flordaguard' rootstock under the ecological conditions prevailing at Attapulgus, Ga. Variations of the usual magnitude and characteristics incident to changes in climatic growing conditions, soils, fertilization, pruning, irrigation, and pest control are to be expected. Colors (except those in common terms) are described from "The Pantone Book of Color" published by H. N. Abrams, Inc., N.Y. 1990.

Tree:

*Ploidy.*—Diploid.

*Size.*—Trees are large when trained to an open vase form.

*Vigor.*—Highly vigorous, and must be summer and winter pruned to keep tree height restricted and to keep center of vase open. Trees respond typically to irrigation and fertilization. Tree growth of 5 to 7 feet in height and 4 to 6 feet in width occurs the first growing season in the field. Annual growth on mature trees averages 2 to 4 feet in length.

*Density.*—Medium to dense in branching habit, and requires pruning to open the tree center which permits high sunlight entrance for enhancing fruit color and sugar.

*Form.*—Semi-spreading and easily pruned to the vase shape.

*Hardiness.*—Hardy with respect to typical south Georgia winters. Chill units estimated at 350 chill units.

*Bearer.*—Trees are precocious and bear fruit on the second leaf in the field. Bearing is annual and without alternate bearing and young fruit must be heavily thinned to avoid limb breakage and to obtain desired fruit size. Trees set several times the number of fruit for a desired crop load.

Trunk:

*Size.*—Medium trunk diameter attaining 15 cm diameter at a height of 30 cm above the ground at the end of 4 years growth at Attapulgus.

*Bark texture.*—Medium smooth, but changes to medium rough as tree ages.

*Bark color.*—Variable with older bark mostly gray, Silver Mink (Pantone 17-1312).

*Lenticels.*—Numerous (15 per 4 square inches of surface area of trunk), small, 5 to 12 mm in length perpendicular to the trunk, and flatoral (while slightly raised, lenticels are flat across the top) shape, being grey, Ash (Pantone 16-3802) in winter.

Branches:

*Size.*—Vigorous growth of scaffold branches. This is not distinctive of the variety.

*Texture.*—Relatively smooth, medium amount of lenticels attaining size found on trunk and old scaffolds. Roughness increases with age.

*Color.*—New wood is light green, Leak Green (Pantone 15-0628); Three-year-old wood is gray, Lead Gray (Pantone 17-1118).

*Blind nodes.*—Moderately low on trees grown at Attapulgus, Ga.

*Crotch angles.*—Angles selected at 45 to 80 degrees in first year of tree training. Natural angles are within the normal range of standard varieties for a semi-spreading tree.

Leaves:

*Size.*—Medium; 14 to 16 cm length, including the petiole; 3 to 4 cm width. Measurements were made on mature leaves in mid-shoot from on vigorous upright summer growth.

*Thickness.*—Regular and average for peach varieties. Not distinctive of the variety.

*Form.*—Lanceolate with an acuminate apex, cuneate base, and serrulate, slightly undulate margin.

*Surface.*—Upper, glabrous; Lower, medium large veins that are pinnately netted.

*Color.*—Lower — Green, Mosstone (Pantone 17-0525); Upper — Green, Avocado (Pantone 18-0430). Veins on lower surface of old leaves and into the petiole shows moderately heavy anthocyanin development in midsummer to autumn as is typical of a 75 to 80 day peach variety.

*Glands.*—Two to occasionally four reniform glands mostly on upper petiole, but occasionally on the base of the leaf blade. Leaf glands are average size and are not distinctive for the variety. Leaf glands on young leaves are light green, Dried Moss (Pantone 14-0626) on young leaves first obtaining full size.

*Petiole.*—About 8 mm (7 to 9 mm) length; 1.3 mm diameter: Light green, Golden Green (Pantone 15-0636) on young leaves of full size in mid summer.

*Stipules.*—Medium in length (6 to 7 mm) and abscising (deciduous) just before leaf obtains full size on summer growth and 2 per node.

*Arrangement.*—Alternate.

Flower buds:

*Hardiness.*—Hardy with respect to south Georgia winters. No damage has been observed at 14 F.

*Abundance.*—Moderately high, most buds set fruit in absence of spring frosts.

*Size.*—Medium, average 3.5 mm length in early winter.

*Form.*—Plump, conic and free.

*Surface.*—Pubescent scales.

*Color.*—Brown, Bitter Chocolate (Pantone 19-1317) in early winter.

Flowers:

*Blossom period.*—Beginning with 'Flordaking' peach — average February 16 to 20 at Attapulgus and occurring over a 7 to 10 day period, dependant on ambient temperatures.

*Aroma.*—Fragrance is slight to none as is typical of most peaches grown for commercial fruit.

*Type.*—Showy, location and seasonally variable, 42 mm average diameter, but within the mid-range size of showy flower in commercial varieties. Petal length, 18 mm average; width, 11 mm average. Petals are obovate and edges vary from smooth to slightly undulate.

*Color.*—Pink, Almond Blossom (Pantone 13-2006) when first open. Upper and lower surface similar color.

*Flower parts.*—Pistil shape and color are withing the range of standard commercial varieties. There are 5 petals and 5 sepals. Sepals are pubescent and petals glabrous. Pistils are usually one per flower and pubescent. Pistil length (from tip of stigma to base of the ovary is 15 to 17 mm and color is light green, Pale Star (Pantone 12-0626). Flower pedicel is 2 to 3 mm length, not distinguishing for the variety.

*Anthers.*—Light red, Jaffa Orange (Pantone 16-1454) at flower opening, darkest when flowers begin opening and fading before pollen is shed, regular size. Size is not uniquely different than that of most self fertile peach varieties.

*Stamens.*—Number varies from 25 to 35. Length is 11 mm.

*Pollen.*—Abundant and bright yellow, Snapdragon (Pantone 13-0840), common to many peach varieties.

*Calyx cup.*—Medium size as compared to commercial varieties. Depth is 4 mm; width at top is 5 mm.

*Fertility.*—Self fertile and no cross pollination is required.

Fruit:

*Maturity when described.*—Tree-ripe, May 8, 2002 at Attapulgus.

*Date of first picking.*—May 6, 2002 at Attapulgus (normal).

*Date of last picking.*—May 12, 2002 at Attapulgus.

*Size.*—Uniform, medium large (large size for early maturity at 120 grams). Varies with number of fiuit per tree, soil type, climatic conditions and cultural practices.

*Average equatorial diameter.*—2¼ inches (58 mm). Slightly wider than height.

*Average polar length.*—2¼ inches (56 mm).

*Pedicel.*—Medium in size: Length is 7 to 9 mm; Width is 3 to 4 mm. Color is yellowish green, Leak Green (Pantone 15-0628). Pedicel is enlarged at point of fruit attachment.

*Longitudinal section form.*—Nearly round.

*Transverse section through diameter.*—Nearly round.

*Suture.*—Shallow and mostly inconspicuous.

*Ventral surface.*—Rounded.

*Base.*—Slightly retuse.

*Apex.*—Round to recessed with no obvious point.

*Cavity at pit.*—None in clingstone fruit.

*Crater at pedicel attachment.*—Flaring circular, but elongated in the suture plane with stem depressing on base of fruit. Depth is 15 mm; Breadth is 25 mm at top and 4 to 5 mm at pedicel attachment.

Skin:

*Thickness.*—Medium in comparison to commercial peach varieties.

*Texture.*—Medium in comparison to commercial peach varieties.

*Tenacity.*—Tenacious to flesh.

*Color.*—Red, Garnet (Pantone 19-1655) over 90 to 100% of skin with darker fine red stripes, Barn Red (Pantone 18-1531) from tip to the shoulder of the fruit. Ground color is deep yellow, Amber (Pantone 14-1045). Fruit exposed to sunlight have a higher degree of enhanced red skin.

*Tendency to crack.*—None observed.

*Taste.*—No astringency observed.

*Pubescence.*—Medium short length and medium soft or less length and less harsh to the touch than occurs on 'Flordaking'.

Flesh:

*Ripens.*—Evenly within each fruit and throughout the tree.

*Texture.*—Firm, fine, juicy, non-melting with few fibers noticeable when fully ripe.

*Fibers.*—Very fine, small, tender and abundant throughout the flesh.

*Aroma.*—Moderate and in the middle range of commercial peach varieties.

*Eating quality.*—Good, sweet, subacid. Fruit range 11 to 13 brix on a refractometer at harvest date. Titratable acidity was 0.64 as % malic acid and the penetrometer firmness with a standard 8 mm tip was 1.6 kg at harvest.

*Juice.*—Abundant.

*Color.*—Yellow, Sulphur (Pantone 14-0755) with some redness, Paradise Pink (Pantone 17-1755) at pit.

*Browning by oxidation.*—Slight on tree ripe fruit beginning to soften.

*Amygdaline.*—Undetected by taste.

Stone:

*Type.*—Clingstone, adhering to flesh even at softening.

*Size.*—Medium small; average length is 27 mm, average width at the equator (dorsal to ventral side) to the suture is 21 mm, average width at the equator perpendicular (facing) the suture is 18 mm, and average pit wall thickness at the equator perpendicular to the suture is 5 mm.

*Color.*—Yellow, Yoke Yellow (Pantone 14-0846) when freshly exposed.

*Form.*—Elliptic shape with an acute base, acuminate tip, and near equal sides.

*Surface.*—Irregularly furrowed toward the ventral edge, pitted from the center toward the base and apex.

*Ridges.*—Slight on the suture.

*Tendency to split.*—Very low.

*Kernel* (*seed*).—Oval shape, bitter (amygdalin is abundant), and viable only with embryo culture. Average width is 10 mm, average length is 14 mm and color is light brown, Hazel (Pantone 17-1143), when first removed from stone of freshly harvested fruit.

Use: Fresh; dessert.

Resistance to disease: High resistance to bacterial spot incited by *Xanthomonas campestris* pv. *pruni* (Smith) Dye. No unusual resistance or susceptibility to insects and diseases noted.

Keeping quality: Excellent after 2 weeks at 2 C, and with minimal bruises or scaring appearing on skin of stored fruit.

Shipping quality: Degree of firmness at harvest and firmness retained in refrigeration for 2 weeks at 2 C with no internal breakdown of flesh or appreciable loss of eating quality indicates fruit should be highly acceptable for shipping.

We claim:

1. A new and distinct peach tree variety as illustrated and described, characterized by a moderate requirement, and bearing early-ripening fruit with firm, yellow and non-melting flesh of high eating quality and an attractive, high percentage red overcolor with fruit ripening in early May or with 'Flordaking' at Attapulgus, Ga.

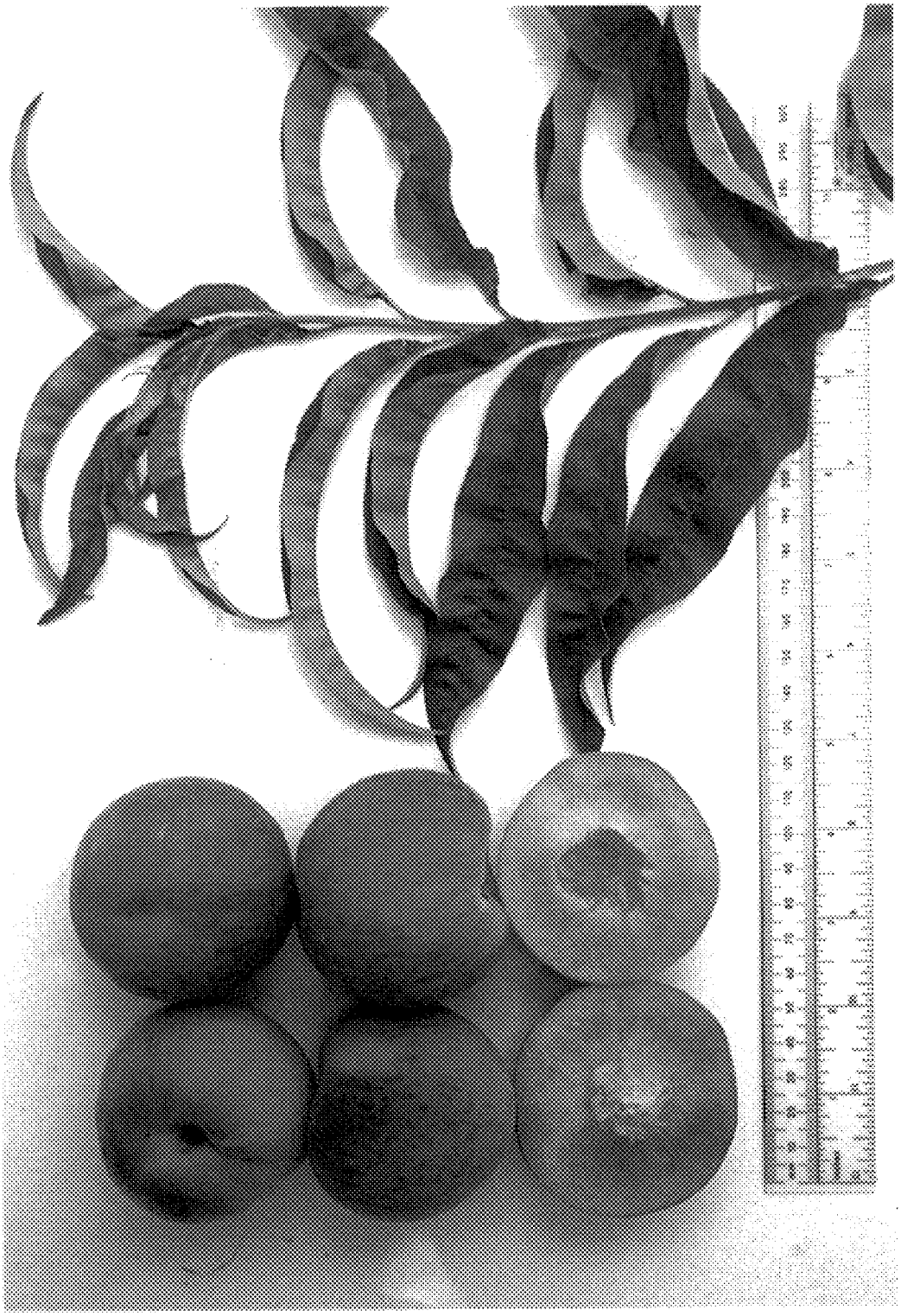

* * * * *